United States Patent [19]

Tse et al.

[11] Patent Number: 5,716,645
[45] Date of Patent: Feb. 10, 1998

[54] TOPICAL FIBRINOGEN COMPLEX

[75] Inventors: Daphne C. Tse, Duarte; Samia S. Mankarious, Costa Mesa; Shu Len Liu, Cerritos; William R. Thomas, Laguna Nigel; Melaine Alpern, Long Beach; Stanley T. Enomoto, Van Nuys; Cataline M. Garanchon, Northridge, all of Calif.

[73] Assignee: Baxter International Inc., Deerfield, Ill.

[21] Appl. No.: 632,922

[22] Filed: Apr. 16, 1996

Related U.S. Application Data

[63] Continuation of Ser. No. 229,158, Mar. 18, 1994, abandoned, which is a continuation-in-part of PCT/US92/07493, Sep. 4, 1992, which is a continuation-in-part of Ser. No. 755,156, Sep. 5, 1991, abandoned.

[51] Int. Cl.⁶ .................................................... A61K 35/16
[52] U.S. Cl. .................. 424/530; 424/94.64; 530/380; 530/381; 530/382; 514/2
[58] Field of Search .................. 424/530, 94.64; 530/380, 382, 381; 514/2

[56] References Cited

U.S. PATENT DOCUMENTS

| | | | |
|---|---|---|---|
| 4,297,344 | 10/1981 | Schwinn et al. | 424/101 |
| 4,442,655 | 4/1984 | Stroetmann | 53/428 |
| 4,453,939 | 6/1984 | Zimmerman et al. | 604/368 |
| 4,495,278 | 1/1985 | Thomas | 435/5 |
| 4,627,879 | 12/1986 | Rose et al. | 106/124 |
| 4,816,251 | 3/1989 | Seelich | 424/101 |
| 4,909,251 | 3/1990 | Seelich | 606/213 |
| 4,928,603 | 5/1990 | Rose et al. | 106/124 |
| 5,030,215 | 7/1991 | Morse et al. | 604/410 |
| 5,099,003 | 3/1992 | Kotitschke et al. | 530/382 |
| 5,138,034 | 8/1992 | Uemura et al. | 530/413 |
| 5,260,420 | 11/1993 | Burnouf-Radosevich et al. | 530/382 |
| 5,272,074 | 12/1993 | Rubers | 435/180 |
| 5,290,552 | 3/1994 | Sierra et al. | 424/94.64 |
| 5,290,918 | 3/1994 | Bui-Khac | 530/381 |
| 5,304,372 | 4/1994 | Michalski et al. | 424/94.64 |
| 5,318,782 | 6/1994 | Weis-Fogh | 424/529 |
| 5,321,126 | 6/1994 | van Donnelin et al. | 530/382 |
| 5,330,974 | 7/1994 | Pines et al. | 514/21 |
| 5,376,631 | 12/1994 | Stet | 514/8 |
| 5,395,923 | 3/1995 | Bui-Khac et al. | 530/381 |
| 5,405,607 | 4/1995 | Epstein | 424/94.64 |
| 5,407,671 | 4/1995 | Heimburger et al. | 424/94.1 |

FOREIGN PATENT DOCUMENTS

| | | |
|---|---|---|
| 408029 | 1/1991 | European Pat. Off. . |
| WO 86/01814 | 3/1986 | WIPO . |

OTHER PUBLICATIONS

Moroi, Masaaki, et al, "Isolation and Characterization of . . . ", *J. Biological Chemistry*, vol. 251, No. 19, pp. 5956–5965, 1976.

*Primary Examiner*—Chhaya D. Sayala
*Attorney, Agent, or Firm*—Janice Guthrie; Michael F. Fedrick

[57] ABSTRACT

A composition which, upon reacting with thrombin, functions as a fibrin sealant and is characterized as being free of detectable levels of lipid enveloped virus activity, free of prothrombin complex and active thrombin, and contains no protease inhibitors or other non-human proteins. Also, described is a method for producing the composition.

15 Claims, 4 Drawing Sheets

TOPICAL FIBRINOGEN COMPLEX

This is a continuation of U.S. application Ser. No. 08/229,158 filed Mar. 18, 1994, now abandoned, which is a continuation-in-part of PCT/US92/07493 filed Sep. 4, 1992 which is a continuation-in-part of U.S. Ser. No. 07/55,156 filed Sep. 5, 1991, now abandoned.

BACKGROUND OF THE INVENTION

1. Field of the Invention

The present invention relates to a fibrinogen composition and its method of preparation, wherein the composition can be used for wound closure in conjunction with thrombin and calcium.

2. Related Art

The attempt to use fibrinogen to achieve topical hemostasis was investigated as far back as the early 20th Century when fibrinogen patches for hemostasis were used in cerebral surgery. Later, mixtures of plasma and thrombin were used for skin grafting and intracavity injections in the therapy of tuberculosis. However, these early attempts had two major drawbacks: since the source of fibrinogen was plasma, the concentration of fibrinogen was low which resulted in a fibrin film of insufficient strength; and it was not possible to inhibit the normal physiologic process of fibrinolysis such that the fibrin film was degraded relatively quickly.

Prior attempts to develop an effective fibrin sealant have also been hampered by the fact that most of these preparations contain high levels of plasminogen which required these compositions to additionally contain an anti-fibrinolytic agent in order to prevent premature degradation of the fibrin seal. Because anti-fibrinolytic agents are typically derived from a non-human source the possibility of a patient having an adverse reaction to such foreign proteins is significant, especially upon multiple exposure to these agents. Although Rose, et al., (U.S. Pat. No. 4,627,879) report the production of a fibrin adhesive which does not necessarily require the presence of an anti-fibrinolytic additive, the composition disclosed in this reference does not deal with another major drawback of these prior fibrin sealing compositions, namely, the possible presence of infectious agents, such as Hepatitis B or HIV, in the plasma. As a consequence, the Rose reference requires that the compositions described therein be derived from a single donor, in order to avoid the transmission of infectious agents which might be associated with pooled plasma.

Thus, there is considerable need for a fibrin sealant which can be derived from pooled plasma and which is free of anti-fibrinolytic compounds, animal proteins, and infectious agents such as viruses. The present invention addresses these needs by providing such compositions.

SUMMARY OF THE INVENTION

The present invention is based upon the discovery that pooled plasma, even when substantially depleted of Factor VIII, can be processed to produce a fibrinogen preparation which, when reacted with thrombin and calcium, will produce a fibrin sealant that can be used to promote hemostasis.

In detail, the invention provides a fibrinogen composition which, in addition to being essentially free of Factor VIII and plasminogen, does not require the use of an anti-fibrinolytic agent and has been treated to eliminate the presence of infectious agents, such as lipid enveloped viruses. A further advantage of the composition is that essentially all of the proteins present in the composition are of human origin.

The composition of the invention, through its transient in vivo presence, provides a matrix which persists for a period of time sufficient to achieve a medical effect, essentially lacks host toxicity upon degradation, and provides mechanical strength to promote hemostasis.

DETAILED DESCRIPTION OF THE PREFERRED EMBODIMENT

Figure 1:
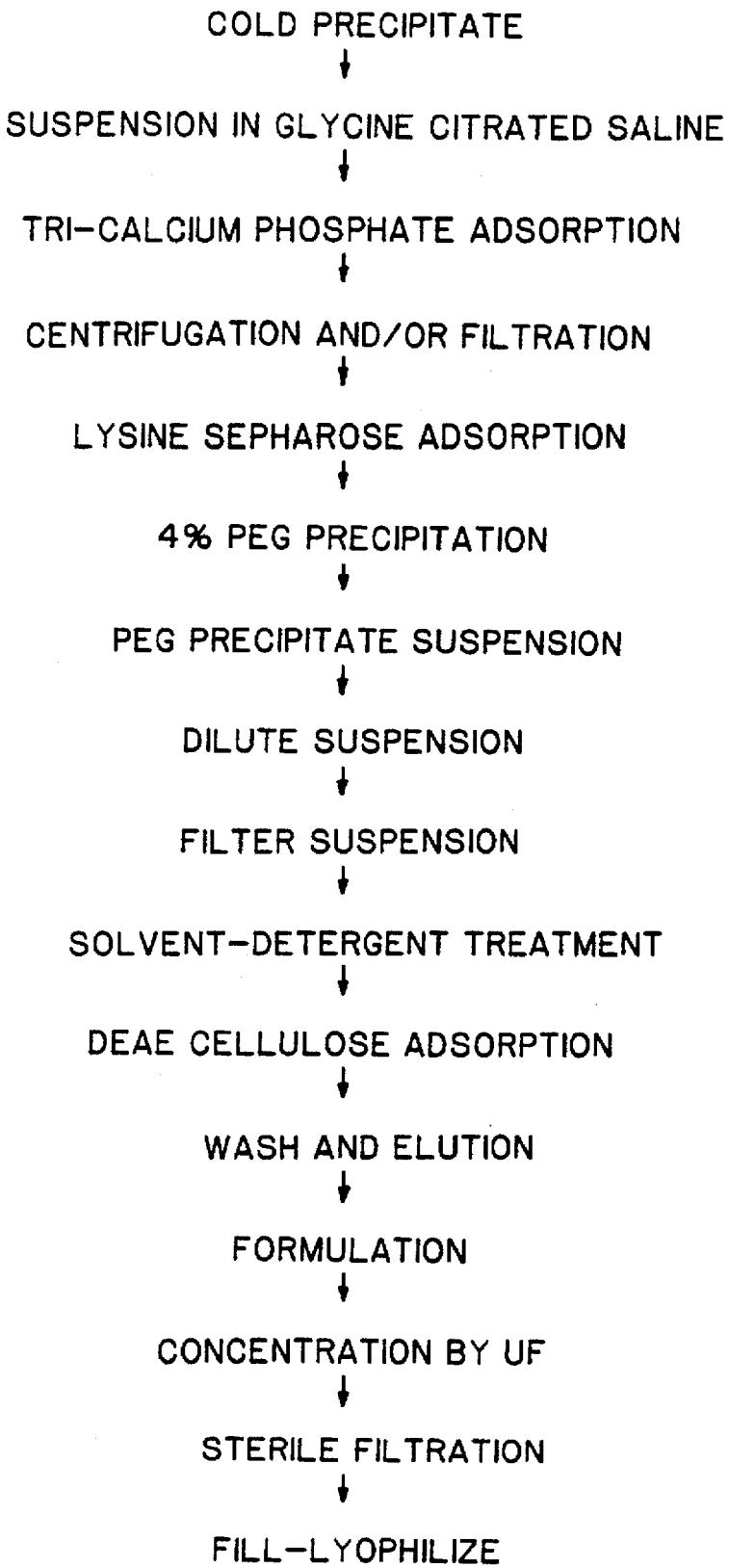
FIG. 1 Schematic representation for preparation of Topical Fibrinogen Complex.

The inventors have devised compositions which, when reacted with thrombin, will produce a fibrin sealant that represents a significant improvement over the prior art compositions intended to accomplish this effect. These compositions (collectively, "Topical Fibrinogen Complex (TFC)"), are advantageous because, like prior art compositions, they will effectively induce hemostasis in human tissue but, unlike prior art compositions, can do so without risk of causing an immunologically adverse response in the treated person to non-human proteins and without substantial risk of viral infection.

Preferred blood fractions for producing the compositions of the invention are plasma, cryoprecipitate, and/or Factor VIII-depleted cold-precipitate. Because the preferred blood fraction for use as a starting material is human plasma, the starting material will hereafter be referred to as plasma, although it will be understood by those of skill in the art that the compositions of the invention can be produced by starting with any human blood-derived fraction which has not been significantly depleted of fibrinogen. Generally, the process involves the formation of a cryoprecipitate from plasma which is high in Factor XIII (F XIII) and fibrinogen. This step may (and preferably will) be followed by cold-precipitation of proteins from the cryoprecipitate. The product of the cold-precipitation process, if any, (i.e, the cold-precipitate), will typically contain a high concentration of fibrinogen and very low levels of F VIII.

More specifically, the preferred method for producing the TFC compositions of the present invention uses frozen human plasma from one or more donors as a starting material. Preferably, the plasma to be used will have been screened using conventional assay techniques for the presence of infectious viral contaminants, such as hepatitis B and human immunodeficiency virus (HIV) to eliminate plasma for use as a starting material which contains detectable levels of such contaminants.

Whether or not the plasma has been previously screened, the cryoprecipitate or cold-precipitate product of the plasma to be used in the compositions of the invention will be treated as further described below to reduce the viral activity therein to undetectable levels. For purposes of this disclosure, the phrase "undetectable levels" will refer to levels of viral activity which can be detected by viral assay protocols which are well known to those of ordinary skill in the art, such as detection of plaque forming units in infected tissue or cells (see, e.g., Example 5). A reduction in the known viral activity level in a given composition will be conventionally described herein as the "$\log_{10}$ reduction factor". Generally, using the available techniques for reducing viral activity in a protein containing composition which are known in the art and/or described herein (see, e.g., Example 5), it can be expected that the compositions of the inventions will have a $\log_{10}$ reduction factor for lipid enveloped viruses of at least 4 logs (preferably at least 6 logs) and a lesser reduction factor for other viral pathogens.

As described in Example 1, to process the frozen plasma to a cryoprecipitate, the plasma is thawed in a controlled environment. The resulting cryoprecipitate may be further processed to TFC without first being converted to a cold-precipitate. However, to limit the total protein content of the compositions of the invention to fibrinogen, residual amounts of fibronectin and any added protein components (such as albumin), the cryoprecipitate will preferably be further processed to a cold-precipitate.

To that end, a cryoprecipitate can be produced by freezing the blood fraction (for example, plasma) which is thereafter warmed to a temperature not exceeding about +6° C. The cryoprecipitate is dissolved in distilled water at about 20° C.–35° C. Calcium chloride is added at a concentrate from about 1 µM to about 1000 µM. Preferably, calcium chloride is added at this step at a concentration of about 40 µM and the pH adjusted to 6.8±0.3 to enhance the precipitation of fibrinogen.

The dissolved cryoprecipitate is then cooled to about 10° C. with mixing, whereupon the cold-precipitate forms. The precipitate is removed from solution by centrifugation at, for example, 5600 g to 7200 g. The precipitate may be stored at –60° C. or lower if desired. Where cold-precipitation is used, the addition of a calcium ion source during the process will enhance the precipitation of fibrinogen, as well as fibronectin, thereby increasing the concentration of these substances in the cold-precipitate. The fibrinogen can also be further concentrated by the addition of polyethylene glycol (PEG) to the cold-precipitate.

The cryoprecipitate or cold-precipitate will usually be dissolved in buffer with mixing and the pH of the cold-precipitate adjusted to about 7.2, preferably to 7.2±0.1. To prevent interaction between the fibrinogen of the cryoprecipitate or cold-precipitate and any thrombin which may be present therein, the cryo- or cold-precipitate will preferably be resuspended in the presence of a protease inhibitor, such as PPACK (D-Phe-L-Pro-L-Arg-chloromethylketone), heparin cofactor II, hirudin or anti-thrombin III (ATIII) to inhibit thrombin which may be present. Most preferred as thrombin inhibitor is PPACK at a concentration from about 0.75 µM to about 1.75 µM. The product of a composition of the invention which has been treated with an effective amount of a thrombin inhibitor will be considered to be essentially free of active thrombin. If used, the thrombin inhibitor will be removed from the compositions of the invention before lyophilization by, preferably, PEG precipitation and, optionally, also the DEAE column step of the procedure (see, FIG. 1 and Example 1). Those of skill in the art will know of other protease inhibitors of thrombin suitable for use in the compositions of the invention and their effective concentrations.

To remove any prothrombin complex which may be present in the cryo- or cold-precipitate, the precipitate suspension is transferred to a buffer solution containing a salt such as tri-calcium phosphate. Exposure to the salt-containing buffer will minimize the likelihood of prothrombin conversion to thrombin which, if such a reaction were to occur, could lead to the conversion of fibrinogen to fibrin. In this state, the resulting composition can be considered to be essentially free of prothrombin complex. The calcium phosphate, in turn, is removed from the process by centrifugation and/or filtration. Additional techniques for removal of prothrombin are described by Murano (*Prothrombin and Other Vitamin K Proteins*, Vol. II, Seegers and Walz, eds., CRC Press, Inc. Boca Raton, Fla., 1986); Heystek, et al., (Vox Sang., 25:113, 1973); Banowcliffe, et al., (Vox Sang., 25:426, 1973); Chandra, et al., (Vox Sang., 41:257, 1981); and Chanas, et al., (U.S. Pat. No. 4,465,623), incorporated herein by reference. Thus, by removing prothrombin and inhibiting thrombin in the compositions of the invention, the final compositions will be essentially free of fibrin molecules; i.e., all of the fibrinogen therein will be unreacted until separately exposed to thrombin (preferably in vivo) to produce a fibrin sealant.

In a preferred embodiment, the dissolved cryo- or cold-precipitate is warmed to about 23°–27° C. and contacted with a lysine affinity column, such as the matrix column product sold commercially under the tradename lysine-Sepharose 4B. Residual plasminogen present in the cryo- or cold-precipitate will be adsorbed by the matrix while fibrinogen will not, thus rendering the resulting solution essentially plasminogen free. For example, using the lysine-Sepharose material referred to above, the resulting final TFC composition will contain no more than 10 µg plasminogen/milliliter of TFC.

The removal of plasminogen is important for two reasons. First, plasiminogen, when converted to plasmin, will break down fibrinogen and fibrin molecules. The latter are formed from interaction between fibrinogen and thrombin in the fibrin sealant to be produced from the compositions of the invention. Second, although fairly effective plasminogen inhibitors are known in the art, their use requires additional manufacturing steps (to determine the concentration of plasminogen present and concentration of inhibitor needed). More importantly, presently commercially available plasminogen inhibitors are of non-human origin and therefore pose the risk of immunologically adverse reactions to compositions which contain them, particularly on repeated applications thereof. This risk is avoided by removal of plasminogen from the compositions of the invention.

The solution collected from the lysine matrix will preferably be concentrated by, for example, the addition of polyethylene glycol (PEG). For use in humans, the PEG used to concentrate the eluate will have a molecular weight in a range which is not toxic to humans (e.g., 3000–6000) and will be added to a final concentration from about 3% to about 7%, preferably about 4% (w/w). Most preferably the resulting PEG precipitate will be dissolved in a buffer solution, filtered and the pH thereof adjusted to an alkaline level; e.g., about 8.6, preferably 8.6±0.1. In an alternate embodiment of the invention, it is also possible to perform the PEG precipitation step prior to adsorption with the lysine matrix.

In all embodiments, the compositions (preferably the concentrated solution) will be treated with an effective amount of a viral activity reducing agent, such as a detergent, which, typically, acts by disrupting the lipid envelope of such viruses as Hepatitis B, HIV, and HTLV. The term "effective amount of viral activity reducing" agent means that the concentration of viral activity reducing agent added to the composition is sufficient to reduce the viral activity in the compositions of the invention to undetectable levels. Of course, the concentration of viral activity reducing agent should not significantly inhibit the ability of the composition to form a fibrin sealant in the presence of thrombin; i.e., the viral activity reducing agent used will not denature fibrinogen.

To some extent, viral contaminants may be removed from the compositions of the invention by virtue of process steps which do not involve the addition of a viral activity reducing agent to the composition. Because viral activity reducing agents typically affect only lipid enveloped viruses (by disrupting the integrity of the lipid envelope), the process steps will likely be the principal means given the current state of the art by which any viruses present which lack a lipid envelope will be removed from the compositions of the invention. Such process steps will be known to, or can readily be ascertained by, one of ordinary skill in the art and include viral partitioning and adsorption/filtration with calcium phosphate.

Nondenaturing detergents which are useful as such agents can be selected by one of ordinary skill in the art from such recognized groups as anionic, cationic, and non-ionic detergents. Examples include sulfated alcohols and sodium acid salts, such as sulfated oxyethylated alkylphenol (sold commercially under the tradenames "Triton W-30" and "Triton X-100"), sodium dodecylbenzensulfonate (sold commercially under the tradename "Nacconol NR"), sodium 2-sulfoethyl oleate (sold commercially under the tradename "lgepon A"), sodium cholate, sodium deoxycholate, sodium dodecylsulfonate, dodecyldimethylbenzylammonium chloride (sold commercially under the tradename "Triton K-60"), oxyethylated amines (sold commercially under the tradename "Ethomeen"), N-dodecylaminoethanesulfonic acid, ethylene oxide-propylene oxide condensates ("Pluronic" copolymers), polyoxyethylated derivatives of esters (sold commercially under the tradenames "Tween 80" and "Polysorbate 80"), polyoxyethylene fatty alcohol ethers (sold commercially under the tradenames "Brij 35"), tetramethylsutylphenyl ethers of polyethylene glycols (sold commercially as "octoxynols"), as well as detergents sold commercially under the tradenames "nonidet P-40" and "Lubrox PX". Those of skill in the art will know of other suitable nonionic detergents for use as all or part of the viral activity reducing agent and may wish to refer, for examples, to U.S. Pat. Nos. 4,481,189, 4,540,573, 4,591,505, 4,314, 997, and 4,315,919.

In the preferred embodiment, the viral activity reducing agent will consist of an organic solvent, preferably tri-n-butyl phosphate (TNBP) mixed with nonionic detergents, preferably polysorbate 80 and octoxynol 9. As described in Examples 1 and 5, undenatured compositions of the invention in which viral activity is at undetectable levels can be produced using a preferred viral activity reducing agent comprised of TNBP (concentration 0.03–0.3%), polysorbate 80 (concentration 0.03–0.3%) and octoxynol 9 (concentration 0.1–1.0%). In addition, chaotropic agents may also be utilized to inactivate viruses, providing the agent does not denature fibrinogen.

Alternatively, the concentration of organic solvent and detergent used in the practice of the preferred embodiments of the invention can vary, depending upon the composition to be treated, and upon the solvent or detergent selected. The alkyl phosphates can be used in concentrations from about 0.10 mg/ml of mixture treated to 1.0 mg/ml, preferably between about 0.1 mg/ml to about 10 mg/ml. The amount of detergent or wetting agent utilized is not crucial since its function is to improve the contact between the organic solvent and the virus. For most of the nonionic materials which are useful, the wetting agent can vary from about 0.001% to 10%, preferably from about 0.01% to about 2% of the aqueous mixture, depending upon the amount of fatty material in the treated aqueous mixture.

Whatever viral activity reducing agent is used, it will be removed after it is contacted with the compositions of the invention for a period of time sufficient to reduce the viral activity in the composition to undetectable levels (at least one minute). In the preferred embodiment, DEAE diethylaminoethyl cellulose (sold commercially under the tradename "DE 52") is the matrix utilized for the removal of the solvent/detergent from the fibrinogen composition. The fibrinogen binds to the diethylaminoethyl cellulose and, after thorough washing to remove unbound material and detergent, is eluted with, for example, 0.3M NaCl. Other ion exchange materials which can be utilized for removal of the solvent/detergent include virtually any of the commercially available anion exchange matrices including, but not limited to, cellulose and agarose matrices. The specific parameters for binding and eluting from these various ion exchange materials are known to those of skill in the art, or can be readily ascertained without undue experimentation.

The stability of the TFC compositions of the invention may be enhanced through the use of such excipients as human serum albumin (HSA), hydroxyethyl starch, dextran, or combinations thereof. The solubility of the compositions may also be enhanced by the addition of a nondenaturing nonionic detergent, such as polysorbate 80. Suitable concentrations of these compounds for use in the compositions of the invention will be known to those of skill in the art, or can be readily ascertained without undue experimentation. The compositions of the invention are, however, sufficiently stable to be stored and used without the use of a stabilizer. Thus, to minimize the non-fibrinogen protein content of the compositions, the most preferred embodiment of the compositions will either contain no added stabilizer or will contain a nonproteinaceous stabilizer. Typically, after formulation the bulk is concentrated from about 20% to about 50% of its original eluate volume, then diluted to the pre-concentration eluate volume. The bulk may then be concentrated to a final total protein concentration of about 4 g ±1 g/dL composition (w/v) before sterile processing and lyophilization. As noted above, a preferred composition of the invention is one which, when reconstituted, will consist essentially of fibrinogen; i.e., the proteins in the composition will be fibrinogen, no more than a residual amount of fibronectin (i.e., 20 mg/ml or less, preferably 10 µg/ml or less), no more than a residual amount of plasminogen (no more than 10 µg/ml, preferably no more than 5 µg/ml) and from about 1 to 40 Units/ml of Factor XIII (preferably more than 10 Units/ml). However, in alternative embodiments of the invention, the composition may also contain components such as a protein stabilizer; e.g., human serum albumin. Thus, the fibrinogen component of the composition may comprise from about 50% to 100% of the total protein in a TFC composition of the invention (w/v), and preferably will comprise at least 75% of the composition (w/v).

In the preferred embodiment, concentration of the protein (s) in the composition is accomplished by ultrafiltration using a membrane with a molecular weight exclusion large enough to allow NaCl to be removed, but small enough to retain protein molecules. This filtration is most preferably performed using a membrane with a 30,000 MW exclusion. When the TFC composition of the invention is lyophilized, the pre-lyophilization volume is usually greater than the volume to which the lyophilizate is resuspended at time of use.

If desired, the compositions of the invention can be modified to include non-proteinaceous as well as proteinaceous drugs. The term "non-proteinaceous drugs" encompasses compounds which are classically referred to as drugs, such as mitomycin C, daunorubicin, and vinblastine, as well as antibiotics.

The proteinaceous drugs which can be added to the fibrinogen compositions of the invention include immuno-modulators and other biological response modifiers. The term "biological response modifiers" is meant to encompass substances which are involved in modifying a biological response, such as the immune response or tissue growth and repair, in a manner which enhances a particular desired therapeutic effect, for example, the cytolysis of bacterial cells or the growth of epidermal cells. Examples of response modifiers include such compounds as lymphokines. Examples of lymphokines include tumor necrosis factor, the interleukins, lymphotoxin, macrophage activating factors, migration inhibition factor, colony stimulating factors, and the interferons. In addition, peptide or polysaccharide fragments derived from these proteinaceous drugs, or independently produced, can also be incorporated into the fibrinogen compositions of the invention. Those of skill in the art will know, or can readily ascertain, other substances which can act as proteinaceous or non-proteinaceous drugs.

The compositions of the invention can also be modified to incorporate a diagnostic agent, such as a radiopaque agent. The presence of such agents allows the physician to monitor the progression of wound healing occurring internally, such as at the liver, gall bladder, urinary tract, bronchi, lungs, heart, blood vessels, and spinal canal. Such compounds include barium sulfate as well as various organic compounds containing iodine. Examples of these latter compounds include iocetamic acid, iodipamide, iodoxamate meglumine, iopanoic acid, as well as diatrizoate derivatives, such as diatrizoate sodium. Other contrast agents which can be utilized in the compositions of the invention can be readily ascertained by those of skill in the art.

The concentration of drug or diagnostic agent in the composition will vary with the nature of the compound, its physiological role, and desired therapeutic or diagnostic effect. The term "therapeutically effective amount" means that the therapeutic agent is present in a sufficient concentration to minimize toxicity, but display the desired effect. Thus, for example, the concentration of an antibiotic used in providing a cytolytic therapeutic effect will likely be different from the concentration of an immune response modulator where the therapeutic effect is to stimulate the proliferation of immune cells at the site of application of the fibrinogen complex. The term "diagnostically effective amount" denotes that concentration of diagnostic agent which is effective in allowing the fibrin glue to be monitored, while minimizing potential toxicity. In any event, the desired concentration in a particular instance for a particular compound is readily ascertainable by one of skill in the art.

The above disclosure generally describes the present invention. A further understanding can be obtained by reference to the following specific examples which are provided herein for purposes of illustration only, and are not intended to be limiting unless otherwise specified.

EXAMPLE 1

PREPARATION OF TOPICAL FIBRINOGEN COMPLEX

Topical fibrinogen complex (TFC) was produced by the initial preparation of a cryoprecipitate of plasma. The cryoprecipitate for such use was prepared by two different techniques depending upon the physical form of the plasma.

In one technique, sealed plastic bottles of frozen plasma were thawed in a controlled environment by contact with a heat exchange medium, such as air or water. The thaw was controlled by programming the temperature and flow of the heat-exchange medium so that the maximum temperature of the plasma did not exceed +6° C. The containers were then opened and the contents pooled into a jacketed stainless steel thawing tank. In the thawing tank, the plasma was gently warmed (while being mixed) to melt the remaining ice. The thawed plasma was then pumped directly to a centrifuge or into a jacketed stainless steel holding tank where it was maintained at 2.5° C.±3.5° C. The plasma was centrifuged to remove the cryoprecipitate. The cryoprecipitate, so prepared, may be stored at or below −25° C. or immediately processed to antihemophilic factor. The cryo-poor plasma was collected in a jacketed stainless steel reaction tank.

Alternatively, cryoprecipitate was prepared by placing sealed plastic bags of frozen plasma in a liquid nitrogen bath for several seconds. The bags were removed from the bath and the crisp, cracked bags were stripped from the plasma. The plasma was then placed into a jacketed stainless steel thawing tank. Alteratively, sealed plastic bags of frozen plasma were arranged so as to warm the bags so that the frozen plasma would break away from the plastic. The containers were then opened and the contents pooled into a jacketed stainless steel thawing tank. In the thawing tank the plasma was gently warmed, while being mixed, to melt the remaining ice. The thawed plasma was pumped directly to a centrifuge or into a stainless steel holding tank where it was maintained at 2.5° C.±3.5° C. The plasma was centrifuged to remove the cryoprecipitate. The cryoprecipitate, so prepared, may be stored at or below −25° C., or immediately be processed to antihemophilic factor. The cryo-poor plasma was collected in a jacketed stainless steel reaction tank.

After the cryoprecipitate was prepared, it was dissolved in distilled water at 20° C. to 35° C. This part of the protocol is illustrated schematically in FIG. 1. Sufficient calcium chloride was added to obtain a minimum calcium concentration of about 40 µM and the pH adjusted to 6.8±0.3. This solution was cooled to 10° C.±2° C. while mixing. The precipitate which forms was removed by centrifugation (5600 g–7200 g). The precipitate may be stored at or below −60° C. or processed directly to TFC. The precipitate was then suspended in Process Solution I at a ratio of four liters of Process Solution I per kg of precipitate. Process Solution I comprises: (a) 0.5M glycine, 0.5M sodium chloride, and 0.1M sodium citrate; pH adjusted to 7.2±0.1 with NaOH, (b)

protease inhibitor: 0.75–1.75 μM PPACK (D-phe-L-pro-L-arg-chloromethyl ketone) or equivalent, and (c) 0.6±0.1 U/ml heparin. The temperature was adjusted to 24°–32° C. and the suspension stirred for approximately one hour.

After the precipitate was suspended in Process Solution I, the suspension was transferred into a tank containing 200 l of process Solution II at 10°–15° C. and stirred for at least 30 minutes. Process Solution II comprises: 7±1 mM sodium phosphate monobasic monohydrate, 18±2 mM sodium phosphate dibasic heptahydrate, calcium phosphate tribasic 0.25% (w/v). The suspension was then allowed to settle undisturbed for at least 30 minutes. The suspension may be centrifuged (5600 g–7200 g) at this step to remove some precipitate. The suspension was then clarified by filtration first through a 0.45μ filter, then through a filter of at least 0.2μ in pore size.

The filtrate was warmed to 23°–27° C. and applied to a Lysine Sepharose 4B column or equivalent. The gel was packed in a chromatography column and equilibrated with 5 column volumes of Process Solution III (25 mM phosphate buffer: 7±1 mM sodium phosphate monobasic monohydrate, 18±2 mM sodium phosphate dibasic heptahydrate).

The unbound material was collected in a tank. The column was washed with at least two gel volumes of Process Solution III. The unbound fractions were pooled. Next, the temperature of the bulk containing the pooled unbound fractions was adjusted to 14±4° C. Polyethylene glycol 3350 was added to a final concentration of 4% (w/w). The suspension was mixed for at least 30 minutes and the precipitate removed by centrifugation (8700 g) at 10°–18° C. The resulting PEG precipitate was dissolved in Process Solution IV (39 mM tris-phosphate with pH adjusted to 8.6±0.1 with phosphoric acid) approximately 15 l/kg precipitate. The protein concentration of the suspension was adjusted to 0.6±0.2 g % (w/v), then the suspension was clarified by filtration. A mixture of Triton X-100, tri (N-butyl) phosphate (TNBP) and Polysorbate-80 was added to the solution to a final concentration of 1.0% (v/v), 0.3% (v/v), and 0.3% (v/v), respectively. The protein-detergent solution was mixed for 1 hour.

The bulk solution was then applied to a chromatography column containing DE 52 ion exchange cellulose resin or equivalent. The resin was packed in a chromatography column and regenerated with 3 column volumes of 1.0M NaCl, then 3 column volumes of 0.5M HCl, 3 column volumes of 0.9% saline, and then 3 column volumes of 0.5M NaOH, and equilibrated with 3 column volumes of 0.5M tris-phosphate buffer (pH adjusted to 8.6), and 3 column volumes of Process Solution IV.

The ion exchange column was then washed with a minimum of 20 column volumes of Process Solution V (0.02M histidine, 0.01M NaCl, pH adjusted to 7.0±0.1 with 6N HCl). The fibrinogen was eluted with Process Solution VI (0.02M histidine, 0.3M NaCl, pH adjusted to 7.0±0.1 with 6N HCl).

The fibrinogen was then supplemented with human serum albumin (5% or 25% human albumin released for therapeutic use) to a concentration of about 80 mg of albumin or less per gram of protein. Polysorbate-80 was added to a final concentration of 15 mg per gram of protein.

Finally, the fibrinogen was concentrated to about 25% of the original volume by ultrafiltration using a 30,000 MW cut-off membrane, then diluted to its preconcentration volume with Process Solution VII (0.02M histidine, pH adjusted to 7.0±0.1). The bulk was again concentrated by ultrafiltration to achieve a final protein concentration of 4±1 g % (w/v). The bulk was sterile filtered (0.2μ), aseptically filled into sterile final containers, lyophilized under aseptic conditions, and closed with sterile closures.

EXAMPLE 2

TFC in vitro STUDIES

A. Clotting Evaluation

Studies were done to determine the TFC composition which will produce fast clotting in the presence of thrombin (i.e., on formation of a fibrin sealant (FS)). Fast clotting was arbitrarily defined as 1–2 seconds. Shorter time periods generally result in clotting within the delivery device and longer times lead to a loose mixture of the components that flows with ill-defined direction.

In performing these experiments, a clean pyrex glass plate was positioned at ~30° from the horizontal axis. A 2" line was drawn on the underside to define the area of FS application.

Human fibrinogen was tested at 50–130 mg/ml total protein with bovine thrombin (Armour Pharmaceutical Co.) at 100–1000 NIH U/ml without $Ca^{++}$. For the purpose of this study the concentration of fibrinogen in the TFC composition was considered to equal the value of total proteins, although it is likely that a residual amount of fibronectin was also present. The effect of adding $[Ca^{++}]$ to a fibrin sealant (TFC, thrombin and calcium salt) was studied at 10, 20, 40, and 60 mM.

The FS was delivered using an experimental dual syringe device (Fenwal) following the 2" line described above, starting at the upper end and moving downward.

Table 1 summarizes the data obtained by testing fibrinogen at 50–130 mg/ml with thrombin at 100–1000 NIH U/ml in the absence of calcium. Each data point is the average of four determinations.

TABLE 1

| AVERAGE CLOTTING TIMES IN SECONDS (±SD) | | | | |
|---|---|---|---|---|
| | Thrombin in NIH U/ml | | | |
| Total Protein (mg/ml) | 100 | 250 | 500 | 1000 |
| 50 | 5.3 ± 1.3 | 2.5 ± 0.4 | 2.3 ± 0.4 | 1.2(N = 1) |
| 90 | 3.8 ± 0.4 | 2.4 ± 0.4 | 1.9 ± 0.4 | 1.4(N = 1) |
| 110 | 5.3 ± 1.6 | 2.2 ± 0.5 | 1.6 ± 0.1 | * |
| 130 | 3.6 ± 0.6 | 1.8 ± 0.2 | 0.8(N = 1) | * |

* Not Determined - clotting occurred too fast for time measurement.
("N" refers to the mean of the 4 measurements made)

As Table 1 shows, clotting times at the lower thrombin concentration (e.g., 100 NIH U/ml) and low protein content (e.g., 50 mg/ml), were long. The mixture was also observed to be "runny". Higher concentrations of thrombin (e.g., 1000 NIH U/ml) generally clotted within the delivery device and therefore were considered unsuitable. Addition of $CaCl_2$ improved the appearance of the clot and generally shortened the clotting time.

Table 2 shows the effect of $[CA^{++}]$ in the range of 0–60 mM. $CaCl_2$ solution was used to reconstitute the thrombin so the final $[Ca^{++}]$, in the 1:1 mixture of FS is half that reported in the Table

TABLE 2

EFFECT OF [Ca++] ON TIME TO CLOT

| Total Protein mg/ml | Thrombin in NIH U/ml | | |
|---|---|---|---|
| | 100 | 250 | 500 |
| 1. [Protein] = 50 mg/ml [calcium ion] | | | |
| 0 mM | 4.3 ± 0.7 | 2.6 ± 0.2 | 2.0 ± 0.6 |
| 10 mM | 2.4 ± 0.3 | 1.8 ± 0.2 | * |
| 20 mM | 2.3 ± 0.2 | 1.2 ± 0.5 | * |
| 40 mM | 2.6 ± 0.2 | * | * |
| 60 mM | 3.0 ± 0.5 | * | * |
| 2. [Protein] = 90 mg/ml [calcium ion] | | | |
| 0 mM | 4.1 ± 1.1 | 2.2 ± 0.2 | 1.8 ± 0.3 |
| 10 mM | 2.9 ± 0.3 | 2.8 ± 0.3 | * |
| 20 mM | 2.0 ± 0.4 | 2.6 ± 0.1 | * |
| 40 mM | 2.5 ± 0.2 | 1.9 ± 0.1 | * |
| 60 mM | 3.2 ± 0.1 | * | * |
| 3. [Protein] = 110 mg/ml [calcium ion] | | | |
| 0 mM | 4.8 ± 1.8 | 2.4 ± 0.5 | 1.7 ± 0.3 |
| 10 mM | 2.9 ± 0.4 | 2.4 ± 1.2 | * |
| 20 mM | 2.6 ± 0.2 | * | * |
| 40 mM | 2.6 ± 0.7 | * | * |
| 4. [Protein] = 130 mg/ml [calcium ion] | | | |
| 0 mM | 3.1 ± 0.8 | 1.5 ± 0.1 | * |

* Not Determined - clotting occurred too fast for time measurement
[Protein] refers to the concentration of total protein in mg/ml TFC.

Based on the above results, it was concluded that a protein range of 90–130 mg/ml and a thrombin concentration of 250–500 NIH U/ml are appropriate for further studies. It was also apparent that additional calcium ion was needed to enhance the clot. Consequently, $Ca^{++}$ concentration was included as a variable in later evaluations.

B. Rate of Cross-Linking

These studies focused on determining the role of Ca ions and the effect of $[Ca^{++}]$ on the extent of fibrin polymerization as well as the rate of cross linking with time due to fibrin polymerization.

The cross-linking reaction of fibrin was tested in a system under reduced conditions which utilized SDS/PAGE. The resolving gels at 7.5% and the stacking gels at 3.75% were cast as described by Schwartz, et al., (*Journal of Clinical Investigation*, 50:1506, 1971).

Thrombin (Armour Pharmaceutical) was reconstituted with or without $CaCl_2$ solution at the desired molarity, i.e., 0, 2, 6, 12, 20, 40, or 60 mM. Fibrinogen was reconstituted with water, quickly mixed with the thrombin in a 12×75 mm test tube and sampled at the appropriate time periods for the studies. The clots were rinsed with 0.15M NaCl then dissolved in three times the clot volume of 9M urea containing 3% SDS and 3% β-mercaptoethanol by boiling in a water bath at 95±5° C. The dissolved clot solutions were then stored at 5° C. until the gel electrophoresis was performed.

The effect of $CaCl_2$ concentration was tested with thrombin at 500 NIH U/ml and fibrinogen at 90 mg/ml and 130 mg/ml after 10 minutes clotting time. The effect of $Ca^{++}$ concentration on the rate of disappearance of the γ-band to form the $_{\gamma-\gamma}$ dimer is shown in FIGS. 2 and 3.

Figure 2:
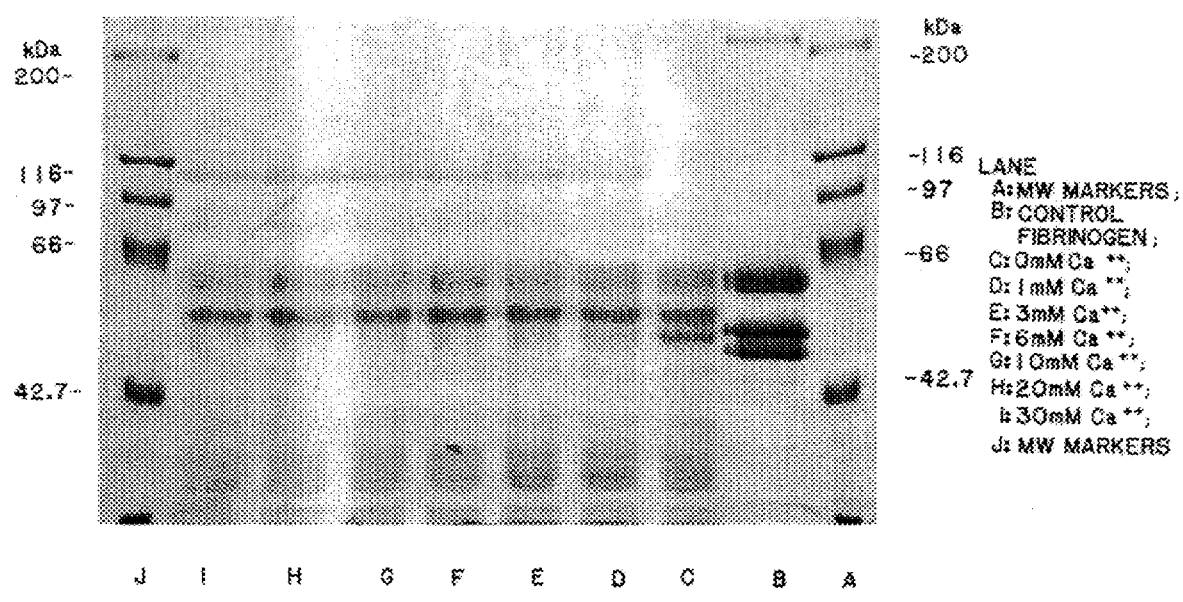
FIG. 2 Effect of calcium ion concentration on fibrin polymer formation. Fibrinogen (90 mg total protein/ml) and thrombin (500 U/ml) were mixed and allowed to incubate for 10 minutes. Lane A: MW markers; Lane B: Control fibrinogen; Lane C: 0 mM $Ca^{++}$; Lane D: 1 mM $Ca^{++}$; Lane E: 3 mM $Ca^{++}$; Lane F: 6 mM $Ca^{++}$; Lane G: 10 mM $Ca^{++}$; Lane H: 20 mM $Ca^{++}$; Lane I: 30 mM $Ca^{++}$; Lane J: MW markers.
Figure 3:
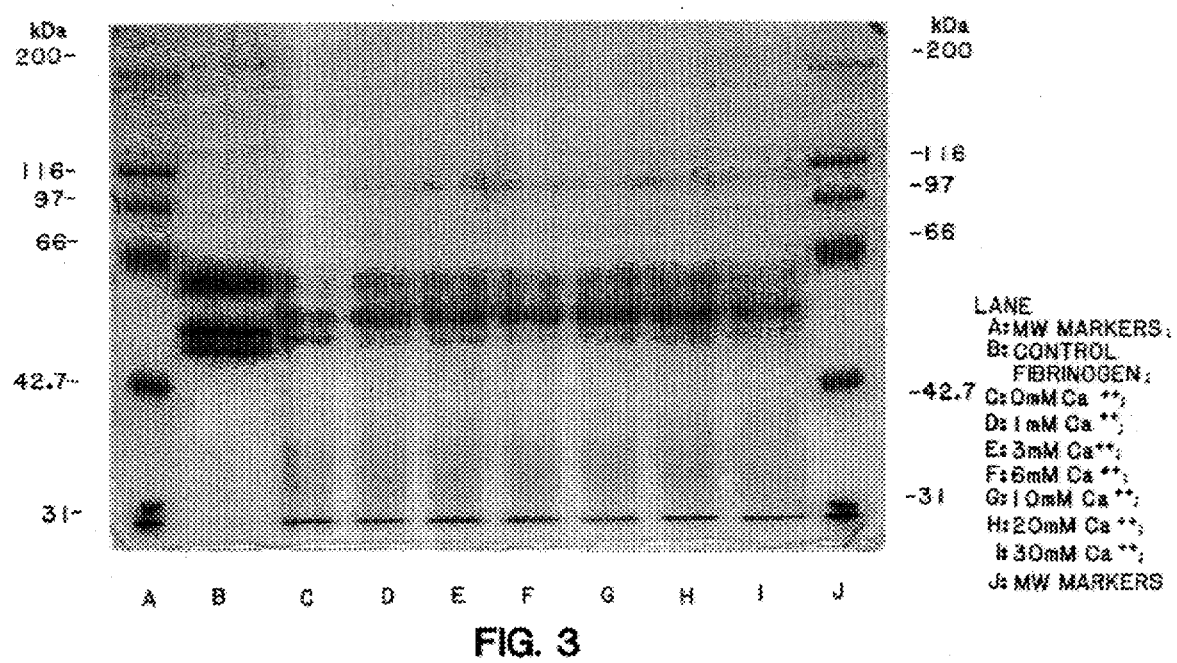
FIG. 3 Effect of calcium ion concentration on fibrin polymer formation. Fibrinogen (130 mg total protein/ml) and thrombin (500 U/ml) were mixed and allowed to incubate for 10 minutes. Lane A: MW markers; Lane B: Control fibrinogen; Lane C: 0 mM $Ca^{++}$; Lane D: 1 mM $Ca^{++}$; Lane E: 3 mM $Ca^{++}$; Lane F: 6 mM $Ca^{++}$; Lane G: 10 mM $Ca^{++}$; Lane H: 20 mM $Ca^{++}$; Lane I: 30 mM $Ca^{++}$; Lane J: MW markers.

As illustrated in FIGS. 2 and 3, the presence of $Ca^{++}$ is necessary for complete fibrin polymerization. As calcium ion in the range of 20–60 mM gives comparable results, a midpoint concentration of 40 mM was chosen to ensure optimal polymerization. Also, there was no significant difference in fibrin polymerization between the two fibrinogen concentrations (90 mg/ml and 130 mg/ml) when measured at the time point studied (10 minutes). Four combinations of thrombin at 250 NIH U/ml or 500 NIH U/ml in 40 mM $CaCl_2$ and fibrinogen at 90 mg/ml or 130 mg/ml were tested to study the effect of varying the concentrations of the components. Samples were taken for gel electrophoresis after 10 minutes of clotting time. Gel electrophoresis of the four combinations of thrombin (in 40 mM $CaCl_2$) and fibrinogen did not reflect any significant differences at the time point studied (10 minutes).

Figure 4:
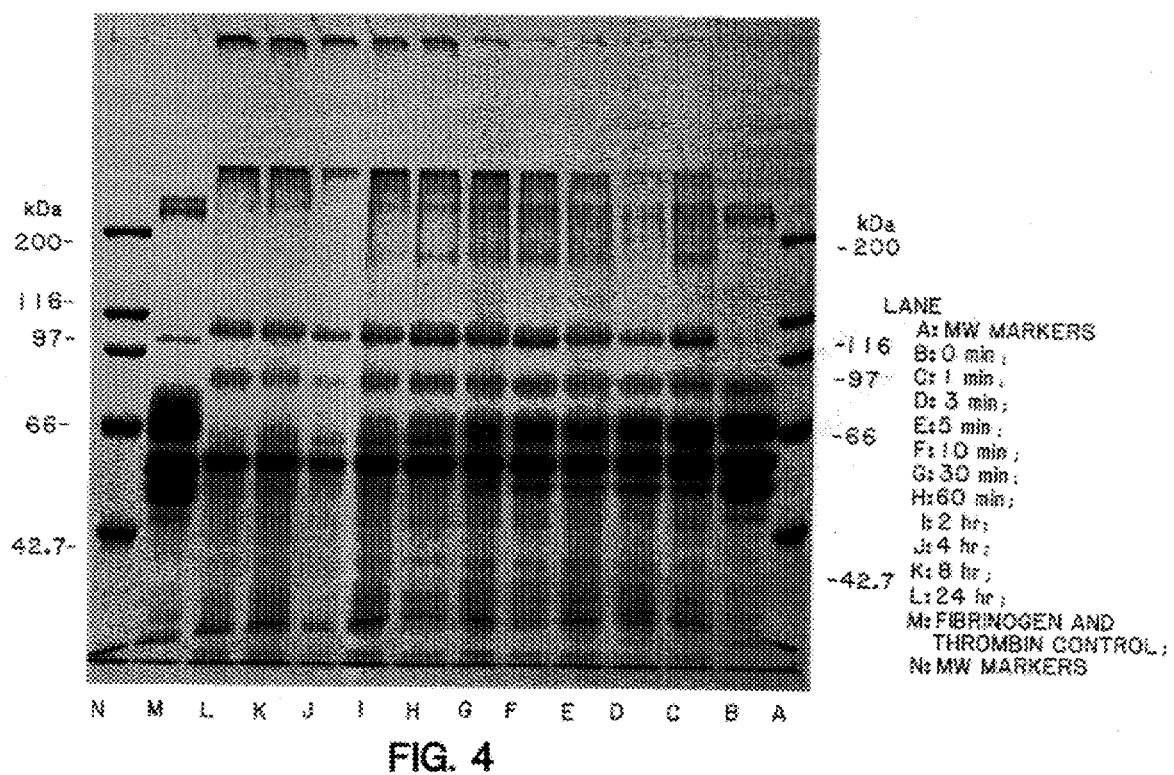
FIG. 4 Rate of fibrin polymerization. Fibrinogen (130 mg total protein/ml) and thrombin (500 U/ml) were mixed in the presence of calcium ion (40 mM $CaCl_2$). Lane A: MW markers; Lane B: 0 min; Lane C: 1 min; Lane D: 3 min; Lane E: 5 min; Lane F: 10 min; Lane G: 30 min; Lane H: 60 min; Lane I: 2 hr; Lane J: 4 hr; Lane K: 8 hr; Lane L: 24 hr; Lane M: fibrinogen control; Lane N: MW markers.

The time study was conducted and sampled over 24 hours. FIG. 4 shows the fibrin polymerization reaction as it progresses through a 24 hour period. Formation of the γ—γ, dimer occurs very rapidly in the presence of $Ca^{++}$ (within one minute) as is shown in FIG. 4. The α polymer is not detectable by this system until 10 minutes incubation time. As the α polymer increases with increasing incubation time (up to 24 hours) the α monomer band shows a corresponding decrease in intensity. To summarize, the time study demonstrates that initial polymerization (γ—γ dimer) occurs almost instantaneously as the reactants are mixed, with the α polymers forming more slowly. From this study it can be concluded that the presence of Ca ion is necessary for polymerization and that the results are similar to those previously reported in the literature (T. Seelich, *J. Head & Neck Pathol.*, 3:65–69, 1982; M. Schwartz, et al., *J. Clinical Inv.*, 50:1506–1513, 1971).

C. Tensile Strength

The tensile strength of the fibrin sealant was evaluated by applying strain to the clot until rupture of the bulk material was observed and measuring the force needed in a tensile stress-strain system. In addition, the change in rupture stress as a function of varying the components in the polymerization mixture used to produce the sealant was studied.

To study the tensile strength of the FS, a mold was designed based on that described by Nowotny, et al., (*Biomaterials*, 2:55, 1981) with some modifications. The newly designed mold was fabricated of transparent plastic to facilitate visual inspection of clot formation. Clotting was allowed to proceed in disposable clot holders for ease of cleaning.

The clot holders were obtained by cutting plastic disposable transfer pipettes (SAMCO, San Fernando Mfg. Co.). Two small pieces of moistened sponge were used to anchor the clotting mixture at both ends. Disposable clot holders with the sponges in place were inserted through the end holders and into the mold, (end holders were included in the mold). A tensiometer instrument (T10, Monsanto) was used to measure and record the peak rupture stress of the clots. Adapters for the T10 grippers were fabricated to hold the end holders.

The clots were formed by injecting equal volumes of fibrinogen and thrombin (with or without $CaCl_2$) using a dual syringe administration device (Fenwal) and a 3 inch 22 gauge needle. All bubbles were removed prior to placing the syringes in their holder. The needle was inserted through one sponge "top", through the mold and into the other sponge "bottom". Parafilm (American Can Co.) placed under the entire mold prevented leakage of excess mixture. As the clotting mixture filled the mold, the needle was withdrawn.

Approximately 2 to 5 minutes before testing, the clot was removed from the mold and placed in the T10 grippers. At testing time, the clot was stretched at a rate of 100 mm/min. The gauge length was set (somewhat arbitrarily) at 6.0 cm and the cross sectional area of the clot was 0.049 cm$^2$. The T10 reported the stress values in Kgf/cm$^2$.

TABLE 3

EFFECT OF CaCl$_2$ ON TENSILE STRENGTH OF FIBRIN SEALANT

| | | Tensile Strength KgF/cm$^2$ | |
|---|---|---|---|
| Fgn.* Conc. mg/ml | CaCl$_2$ mMol | @ 250 NIH U/ml Thrombin (N) | @ 500 NIH U/ml Thrombin (N) |
| 90 | 0 | 0.93 ± 0.136 (9) | 1.23 ± 0.165 (8) |
| 110 | 0 | 1.07 ± 0.150 (10) | 1.29 ± 0.237 (9) |
| 130 | 0 | 0.94 ± 0.157 (14) | 1.36 ± 0.177 (16) |
| 90 | 10 | 1.65 ± 0.380 (12) | 1.92 ± 0.350 (8) |
| 110 | 10 | 2.60 ± 0.540 (8) | 2.80 ± 0.610 (8) |
| 130 | 10 | 2.35 ± 0.760 (11) | 3.24 ± 1.170 (8) |
| 90 | 20 | 1.65 ± 0.406 (8) | 2.15 ± 0.540 (8) |
| 110 | 20 | 2.26 ± 0.530 (8) | 4.11 ± 1.080 (8) |
| 130 | 20 | 2.23 ± 0.489 (8) | 3.54 ± 1.030 (8) |
| 90 | 40 | 1.74 ± 0.410 (8) | 2.36 ± 0.390 (11) |
| 110 | 40 | 2.36 ± 0.660 (8) | 3.79 ± 0.626 (8) |
| 130 | 40 | 2.63 ± 0.670 (12) | 4.05 ± 0.940 (9) |
| 90 | 60 | 2.10 ± 0.38 (8) | 2.29 ± 0.450 (8) |
| 110 | 60 | 3.00 ± 0.690 (8) | 4.13 ± 0.896 (8) |
| 130 | 60 | 3.69 ± 0.787 (10) | 3.57 ± 1.160 (9) |

*Fibrinogen Lot #2830R129

Measurements of tensile strength (peak stress) were taken 10 minutes after injection of the clotting mixture. The results in Table 3 show the effect of varying the CaCl$_2$ concentration when thrombin is 250 NIH U/ml or 500 NIH U/ml. Three concentrations of fibrinogen (90, 110, and 130 mg total protein/ml) were tested. Each measurement of peak stress was the average of N determinations. A minimum of 8 readings were taken per point.

As shown in Table 3, in the absence of Ca$^{++}$, the clots had the lowest peak stress values at both thrombin concentrations and at all fibrinogen levels. Addition of calcium ions at 10-60 mM increased the tensile strength for all thrombin/fibrinogen concentrations. Generally, higher values were observed at the higher thrombin concentration, i.e., 500 NIH U/ml of thrombin, which also gave somewhat similar values for [Ca$^{++}$] in the range of 20-60 mM of calcium ions. The lowest standard deviation (SD) values were observed at 40 mM CaCl$_2$.

A second lot of human fibrinogen was tested to confirm these findings and the data were compared at 40 and 60 mM CaCl$_2$ and 500 NIH U/ml thrombin. The results of testing a second lot of fibrinogen showed generally similar values of peak stress particularly at the higher fibrinogen concentrations of 110 and 130 mg/ml and also showed higher values at 90 mg/ml.

Time studies of the clot tensile strength were performed over a 24 hour time period using fibrinogen at 90 mg/ml and 130 mg/ml with thrombin concentration at 500 NIH U/ml and CaCl$_2$ at 40 mM. Over a 24 hour period, the tensile strength showed no significant decrease in value. A gradual increase in peak stress was expected to occur as cross linking continued with time.

D. Clot Lysis Studies

The length of time that a fibrin clot will remain solid when incubated at 37° C. under sterile, moist conditions, with and without a plasminogen activator, was determined. Also tested was the effect on the clot longevity of adding protease inhibitor (Aprotinin) to the reaction mixture.

Sterile human fibrinogen solution was prepared using one of the following diluents:
  a. sterile water (i.e., zero KIU/ml Aprotinin)
  b. Aprotinin solution at 1000 KIU/ml
  c. Aprotinin solution at 3000 KIU/ml
to yield one of three concentrations; 90, 110, or 130 mg/ml of total protein.

Thrombin was prepared by reconstituting with a 40 mM CaCl$_2$ solution to produce either a 250 or 500 NIH U/ml. Thus, six combinations of thrombin and fibrinogen were tested. Urokinase (Abbott) was prepared at 5 U/ml in normal saline.

Fibrin clots were formed by mixing equal volumes of fibrinogen (in H$_2$O or Aprotinin) and thrombin (in CaCl$_2$ solution) in cylindrical silicone tubing (5 mm inner diameter). The mixture was delivered using a dual syringe administration device (Fenwal). All the delivery devices and the silicone tubing were sterilized by autoclaving.

A 10 cm length of silicone tubing was sealed at one end using parafilm. Holding the tubing about 10° from vertical, the Fenwal device was used to inject the fibrinogen and thrombin rapidly into the tubing with the (22 g) needle tip barely penetrating the parafilm. After the clot had solidified for 20 minutes, the 10 cm silicone tubing was cut into 3 cm lengths to yield a clot volume of 590 µl. Each 3 cm segment was cut in half and the two halves were placed in one well of a sterile 24-well plate (Corning). Any segment that was found to contain air bubbles was discarded. The clot was extruded from the tubing by gently squeezing the tube at one end. It was rinsed with 1 ml of sterile saline then 1 ml of either urokinase or saline was added to the well and the plate was placed in a sterile, moist, 37° C. incubator. Every 24 hours, the supernatants from each well were removed for testing using the Fibrin(ogen) Degradation Products agglutination kit (Baxter Dade).

The urokinase and saline solutions were replaced daily with fresh reagents before returning the plate to the 37° C. incubator. All preparations and sampling of supernatants were performed under sterile conditions. The clots were visually inspected and their appearance noted. After 14 days the experiment was terminated. Total number of conditions tested was 36 and all conditions were performed in duplicate.

TABLE 4

CLOT LYSIS TIMES
[+ UROKINASE, NO APROTININ]

| CONDITION | TIME CLOT LOST CYLINDRICAL SHAPE |
|---|---|
| 130 mg/ml fibrinogen + 500 U/ml thrombin | Day 10 |
| 130 mg/ml fibrinogen + 250 U/ml thrombin | Day 8 |
| 110 mg/ml fibrinogen + 500 U/ml thrombin | Day 7 |
| 110 mg/ml fibrinogen + 250 U/ml thrombin | Day 11 |
| 90 mg/ml fibrinogen + 500 U/ml thrombin | Day 8 |
| 90 mg/ml fibrinogen + 250 U/ml thrombin | Day 8 |

Table 4 summarizes the clot lysis time (defined as the time clots lost their cylindrical shape) in the presence of urokinase when no Aprotinin was included. The observed range was 7-11 days with a mean of 8.66±1.5d. Measurements of Fibrin(ogen) Degradation Products (FDP) showed a peak in activity that generally corresponded to or soon followed the time when the clots lost their well-defined shape.

When urokinase was deleted and the clots were incubated in normal saline only, in presence or absence of Aprotinin, the clots maintained their integrity during the entire observation period (i.e., 14 days). FDP measurements confirmed the absence of significant clot lysis.

This study shows that when the clot is not influenced by any plasminogen activators in situ, it should be expected to last for at least 14 days. When urokinase is present, the clots last a minimum of 7 days. These time periods may be sufficient for the healing mechanism to play its natural role.

Thus, based on these results, it can be concluded that the trace levels of plasminogen in the fibrinogen preparations do not adversely affect the clot longevity and that the addition of a protease inhibitor, such as Aprotinin, is not necessary.

EXAMPLE 3

TFC in vivo TESTING

Studies were done to evaluate the optimal concentration of TFC using an in vivo model. Swiss Webster mice (20–25 g) were arranged in 10 groups of five for testing. In the protocol which was utilized, each animal was anesthetized, weighed, and a small piece of skin was removed from the back of the animal. The skin specimen was dipped in a saline solution and attached to a Gottlob device. Equal volumes of TFC and thrombin at various concentrations (Table 2) were then added simultaneously to the wound, the skin replaced onto the animal, and held in place for approximately two minutes.

The anesthetized animal was placed face down on a platform which was then positioned on a tensiometer (Monsanto Company) and the Gottlob device attached to the grippers. The tensiometer parameters were set to: (1) area: 1.76 cm$^2$; (2) speed: 10.0 mm/min.; (3) gauge: 1.0 cm; (4) stress range: 500.0%. The force required to separate the piston (with the skin specimen) from the back of the animal was recorded in g/cm$^2$. The data from these experiments were statistically evaluated using RS1/Discover software (BBN Software Corp., Cambridge, Mass.). Analysis of the results of this study indicated that TFC at 120–130 mg/mL and thrombin at 250 U/mL gave maximal adhesion responses.

The ability of the clot to adhere to tissue in vivo is important in maintaining hemostasis. In this experiment, a maximum adhesion response occurred within the range of reagents tested, confirming the in vitro findings of Example 2.

EXAMPLE 4

CHARACTERISTICS OF TFC

A TFC composition was prepared generally according to the process steps described in Example I. The characteristics of TFC identified below were analyzed with the following results:

TABLE 5

| TEST | RESULTS |
| --- | --- |
| SOLUBILITY | 1050 seconds |
| pH | 7.2 |
| STERILITY | STERILE |
| PYROGEN | NON-PYROGENIC |
| HEPATITIS B (HBsAg) | NON-REACTIVE |
| TOTAL PROTEIN | 10.4 g/dL |

TABLE 5-continued

| TEST | RESULTS |
| --- | --- |
| CLOTTABLE PROTEIN | 86% |
| F-XIII | 32.4 U/ml |
| PLASMINOGEN | <0.1 mg/dL |
| PEG | 0.0 g/dL |
| TRITON X-100 | 0.4 PPM |
| TNBP | 1.1 PPM |
| TWEEN-80 | 0.1% |
| ALBUMIN | 0.64 g/dL |
| HISTIDINE | 55.9 mM |
| SODIUM | 213 mg/L |

EXAMPLE 5

REDUCTION OF VIRAL ACTIVITY IN TFC PROCESS INTERMEDIATES TO UNDETECTABLE LEVELS

TFC process intermediates (see, Example 1) were assayed for activity of 5 lipid enveloped viruses. The lipid enveloped viruses assayed were: *Pseudorabies* ("PRV", as a model for herpes viruses), HIV Types 1 and 2, *Sindbis* ("SIN", as a model for hepatitis C virus), and *Vesicular Stomatis Virus* ("VSV", as a model for RNA viruses). The process intermediates were obtained after the resuspension of PEG precipitate in tris-phosphate buffer, pH 8.6±0.3 (without buffer, the viricidal activity of the viral activity reducing agent would be reduced and an agent of greater concentration would be used).

For purposes of the assay, the samples were separately spiked with four lipid enveloped viruses in the presence of the following viral activity reducing agent: a mixture of TNBP, octoxynol 9 and polysorbate 80, in respective ratios of 0.3%:1%:0.3% (v/v).

PRV, VSV and SIN were assayed by incubation with appropriate cell lines (porcine kidney 13 ("PK-13"), buffalo green monkey kidney ("BGMK") and Vero, respectively) to determine plaque forming units ("pfu") before and after treatment with the viral activity reducing agent. HIV-1 was assayed by incubation with susceptible T cells (H9) to determine 50% of the tissue culture infectious dose end point (TCID$_{50}$) of the virus before and after treatment with the viral activity reducing agent. The results of these assays are tabulated below, which demonstrate that the use of the viral activity reducing agent during the manufacture of TFC is very effective in reducing the activity of lipid envelope viruses therein.

TABLE 6

| | VIRUS RECOVERY | | | |
| --- | --- | --- | --- | --- |
| | LOG$_{10}$ TCID$_{50}$ | Log$_{10}$ pfu/mL | | |
| | HIV-1 | VSV | PRV | SIN |
| Virus + TFC Solution | 12.5 | 9.0 | 8.9 | 8.9 |
| Virus + TFC Solution After Incubation | Negative | <1.9 | <1.9 | <1.9 |
| Log$_{10}$ Reduction Factor | 12.5 | 7.1 | 7.1 | 6.9 |

No plaques were detected. The theoretical detection point of the assay was used to calculate the virus recovery. Reagent cytotoxicity due to solvent/detergent mixture (i.e., the viral activity reducing agent) has been taken into account for these calculations.

EXAMPLE 6

PYROGENICITY OF TFC

The pyrogenicity of the TFC composition of Example 4 was tested using the well known rabbit pyrogen test. Three rabbits were injected with a dose of 0.5 ml/kg and their body temperatures monitored over a course of three hours following the injection. The results of this test are tabulated below, which strongly indicate that TFC is non-pyrogenic.

TABLE 7

| # | Rabbit Weight (kg) | Dose (ml) | Pre-injection Temperature (°C.) | TEST TEMPERATURE (°C.) | | | Maximum Rise (°C.) |
|---|---|---|---|---|---|---|---|
| | | | | 1 hr | 2 hr | 3 hr | |
| 1 | 3.23 | 1.7 | 39.2 | 39.1 | 39.1 | 39.1 | 0.0 |
| 2 | 2.70 | 1.4 | 39.1 | 39.0 | 39.0 | 39.1 | 0.0 |
| 3 | 3.11 | 1.6 | 39.6 | 39.5 | 39.5 | 39.5 | 0.0 |
| | | | | Sum of Maximum Rise: | | | 0.0 |

The preceding examples and description are provided to assist in understanding the present invention and, as such, are intended to be exemplary only, not limiting. Those of skill in the art will recognize that other materials or methods may be used, depending on the circumstances, and still remain within the spirit and scope of the present invention.

We claim:

1. A hemostasis promoting composition derived from human plasma or plasma fractions wherein:
   (a) fibrinogen comprises at least 50% of the total protein concentration;
   (b) F XIII is present at a concentration of about 10 to about 40 units/ml;
   (c) the composition is free of detectable levels of lipid enveloped virus activity;
   (d) the composition is non-pyrogenic;
   (e) plasminogen is present at a concentration no higher than 5 µg/ml;
   (f) prothrombin complex and active thrombin are not detectable; and
   (g) the composition is free of fibrinolysis inhibitors.

2. The composition of claim 1, wherein the composition is lyophilized.

3. The composition of claim 1, which further comprises a stabilizer.

4. The composition of claim 1, which further comprises a therapeutically effective amount of a drug.

5. The composition of claim 1, which further comprises a diagnostically effective amount of a diagnostic agent.

6. A fibrin sealant comprising a mixture of:
   i. a hemostasis promoting composition derived from human plasma or plasma fractions wherein:
      (a) fibrinogen comprises at least 50% of the total protein concentration;
      (b) F XIII is present at a concentration of about 10 to about 40 units/ml;
      (c) the composition is free of detectable levels of lipid enveloped virus activity;
      (d) the composition is non-pyrogenic;
      (e) plasminogen is present at a concentration no higher than 5 µg/ml;
      (f) prothrombin complex and active thrombin are not detectable; and
      (g) the composition is free of fibrinolysis inhibitors,
   ii. a catalytically effective amount of thrombin; and,
   iii. calcium ion.

7. The composition of claim 1, which further comprises a solubilizer.

8. The composition of claim 1 wherein plasminogen is present at a concentration less than 1 µg/ml.

9. The composition of claim 6 wherein the composition is lyophilized.

10. The composition of claim 8 which further comprises a therapeutically effective amount of a drug.

11. The composition of claim 8 which further comprises a diagnostically effective amount of a diagnostic agent.

12. The composition of claim 8, which further comprises a stabilizer.

13. The composition of claim 8, which further comprises a solubilizer.

14. A hemostasis promoting composition derived from human plasma or plasma fractions wherein:
   (a) fibrinogen comprises at least 50% of the total protein concentration;
   (b) the composition is free of detectable levels of lipid enveloped virus activity;
   (c) the composition is non-pyrogenic, and;
   (d) plasminogen is present at a concentration no higher than 5 µg/ml.

15. The composition of claim 14 wherein plasminogen is present at a concentration less than 1 µg/ml.

* * * * *